(12) United States Patent
Asfora (10) Patent No.: US 6,419,678 B1
(45) Date of Patent: Jul. 16, 2002

(54) CURVED DRILL GUIDE SYSTEM

(76) Inventor: Wilson T. Asfora, 1500 W. 22nd St. Suite 101, Sioux Falls, SD (US) 57105

(*) Notice: Subject to any disclaimer, the term of this patent is extended or adjusted under 35 U.S.C. 154(b) by 0 days.

(21) Appl. No.: 09/723,975

(22) Filed: Nov. 28, 2000

(51) Int. Cl.⁷ .............................................. A61B 17/90
(52) U.S. Cl. ...................................................... 606/96
(58) Field of Search ...................... 408/97, 705, 241 G; 606/96, 98, 80, 53, 1; D24/140

(56) References Cited

U.S. PATENT DOCUMENTS

| | | | |
|---|---|---|---|
| 3,819,099 A | * 6/1974 | Bierendeld | 226/91 |
| 4,312,337 A | * 1/1982 | Donohue | 128/92 EB |
| 4,337,761 A | * 7/1982 | Upsher | 128/11 |
| 4,798,213 A | * 1/1989 | Doppelt | 128/754 |
| 5,312,412 A | * 5/1994 | Whipple | 606/96 |
| 5,443,474 A | 8/1995 | Sfakianos et al. | |
| 5,624,447 A | * 4/1997 | Myers | 606/96 |
| 5,840,013 A | * 11/1998 | Lee et al. | 600/114 |
| D404,126 S | 1/1999 | Asfora | |
| 5,951,561 A | * 9/1999 | Pepper et al. | 606/80 |
| 6,074,392 A | * 6/2000 | Durham | 606/67 |
| 6,309,396 B1 | * 10/2001 | Ritland | 606/96 |

OTHER PUBLICATIONS

Ronald I. Apfelbaum, MD, "Anterior Screw Fixation of Odontoid Fractures," Neurosurgical Operative Atlas, The American Association of Neurological Surgeons (Date unknown), vol. 2 ( No. 3), pp. 189–199, ( Nov. 1, 1992).

* cited by examiner

Primary Examiner—Eduardo C. Robert
(74) Attorney, Agent, or Firm—Kaardal & Leonard, LLP; Jeffrey A. Proehl (57) ABSTRACT

A curved drill guide system for forming a channel in a vertebra of a patient for receiving a screw. The curved drill guide system includes an elongate handle member for being held by the hand. A mounting aperture extends through the handle member, with the mounting aperture having an axis oriented perpendicular to a longitudinal axis of the handle member. A guide member is provided for removably receiving and guiding the flexible drill bit. The guide member comprises a guide tube adapted for removably inserting into the aperture of the handle member. The guide tube has a base end and a free end and a length therebetween. A bore extends along the length of the guide tube and open at the base and free ends. The guide tube has an arcuate shape, with the arcuate shape being substantially uniform along the length of the guide tube.

20 Claims, 5 Drawing Sheets

CURVED DRILL GUIDE SYSTEM

BACKGROUND OF THE INVENTION

1. Field of the Invention

The present invention relates to surgical drill guides and more particularly pertains to a new curved drill guide system for forming a channel in a vertebra of a patient for receiving a screw for screw fixation of a fracture.

2. Description of the Prior Art

The invention is directed to the treatment of fractures of the odontoid process from the body of the second cervical vertebra of a patient. The odontoid process is a tooth-like protrusion of bone extending upwardly from the body of the second cervical vertebra and it forms a pivoting joint with the first cervical vertebra for permitting the head of a person to rotate generally about the longitudinal axis of the body.

In particular, hyperflexion or hyperextension of the head can cause a type II odontoid fracture which generally occurs across the base of the odontoid process at the general location where the odontoid process meets the body of the second cervical vertebra.

One treatment of the type II fracture of the odontoid process involves anterior screw fixation, in which a channel is formed in a generally upward direction through an inferior surface of the second cervical vertebra and into the body of the second cervical vertebra, through the fracture line and into the odontoid process. Once the channel has been formed, the channel is tapped with threads and a screw is then threaded into the channel to secure the odontoid process to the body of the second cervical vertebra. One illustrative description of such a procedure is set forth by Ronald I. Apfelbaum, M.D. in ANTERIOR SCREW FIXATION OF ODONTOID FRACTURES, *Neurological Operative Atlas*, Vol. 2, No. 3, 1992, pages 189–199.

The channel has typically been formed using a rigid drill bit inserted through a straight drill guide extending through an anterior incision in the patient's neck. However, using this apparatus for this surgical technique is difficult, if not impossible, in some patients, especially those that have very short necks, very large necks, or very prominent anterior chest walls. In these cases, the rigid drill bit with the straight drill guide cannot be oriented at a suitable angle for forming the channel through the body and odontoid process of the second cervical vertebra. Almost invariably, another treatment approach must then be utilized.

The curved drill guide system according to the present invention substantially departs from the conventional concepts and designs of the prior art, and in so doing provides an apparatus primarily developed for the purpose of forming a channel in a vertebra of a patient for receiving a screw for screw fixation of a fracture.

SUMMARY OF THE INVENTION

In view of the foregoing disadvantages inherent in the known types of surgical drill guides now present in the prior art, the present invention provides a new curved drill guide system construction wherein the same can be utilized for forming a channel in a vertebra of a patient for receiving a screw for screw fixation of a fracture.

The general purpose of the present invention, which will be described subsequently in greater detail, is to provide a new curved drill guide system which has many of the advantages of the surgical drill guides of the prior art and many novel features that result in a new curved drill guide system.

The present invention generally comprises an elongate handle member for being held by the hand. A mounting aperture extends through the handle member, with the mounting aperture having an axis oriented perpendicular to a longitudinal axis of the handle member. A guide member is provided for removably receiving and guiding a flexible drill bit. The guide member comprises a guide tube adapted for removably inserting into the aperture of the handle member. The guide tube has a base end and a free end and a length therebetween. A bore extends along the length of the guide tube and open at the base and free ends. The guide tube has an arcuate shape, with the arcuate shape being substantially uniform along the length of the guide tube.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The various objects and features of novelty which characterize the invention are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
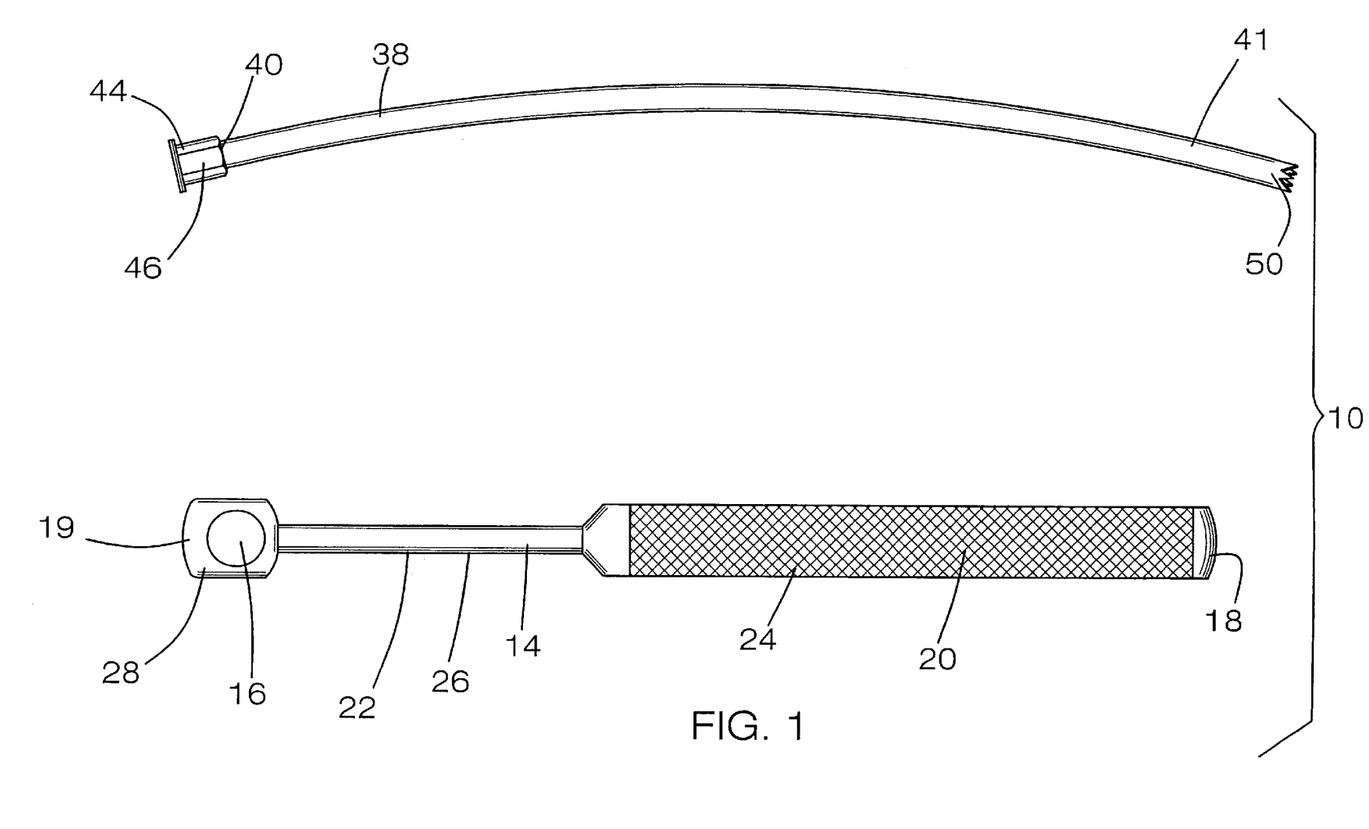
FIG. 1 is a schematic side view of the handle member and the guide member of a new curved drill guide system according to the present invention in a disassembled condition.
Figure 2:
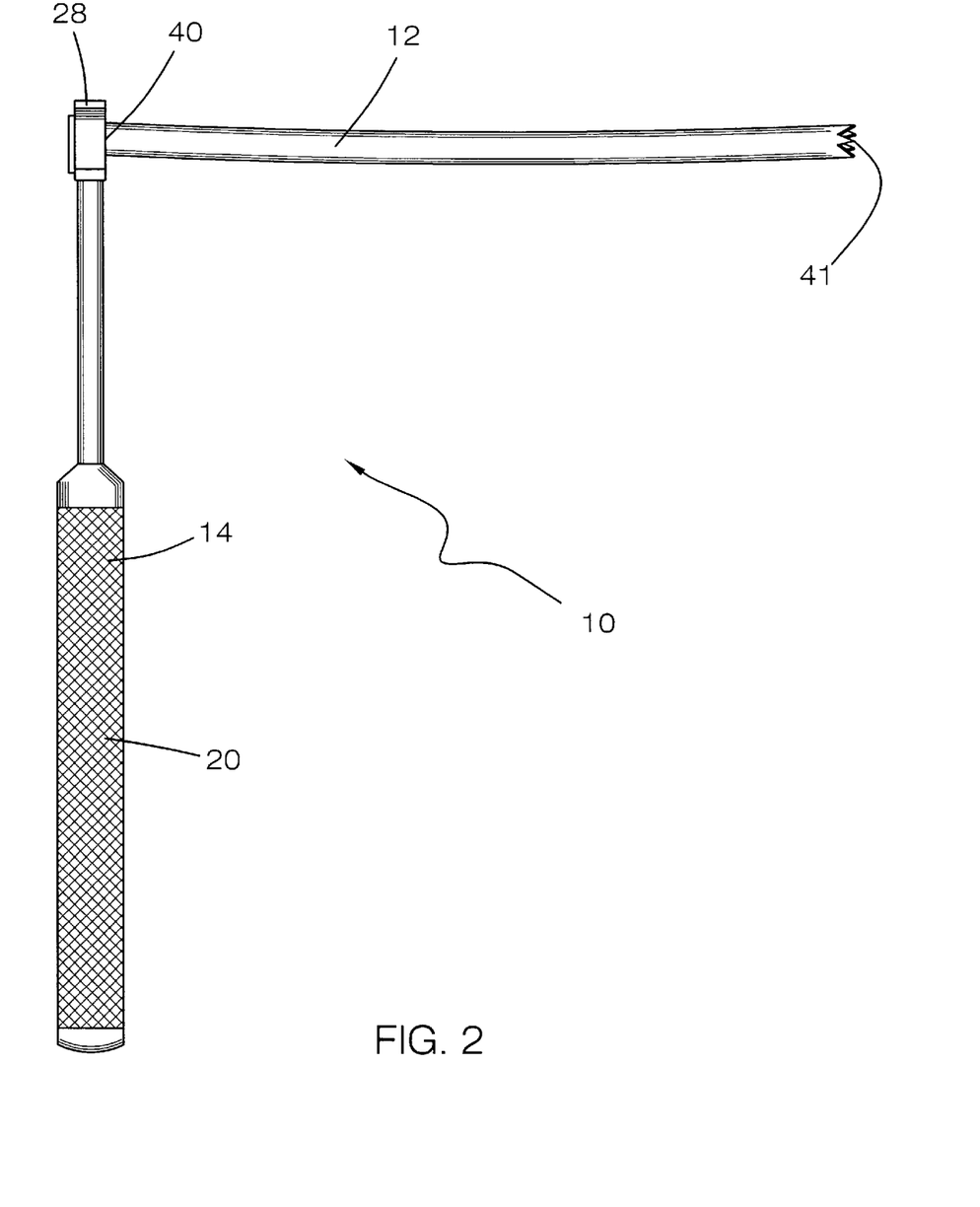
FIG. 2 is a schematic side view of the handle member and guide member of the present invention in an assembled condition.
Figure 3:
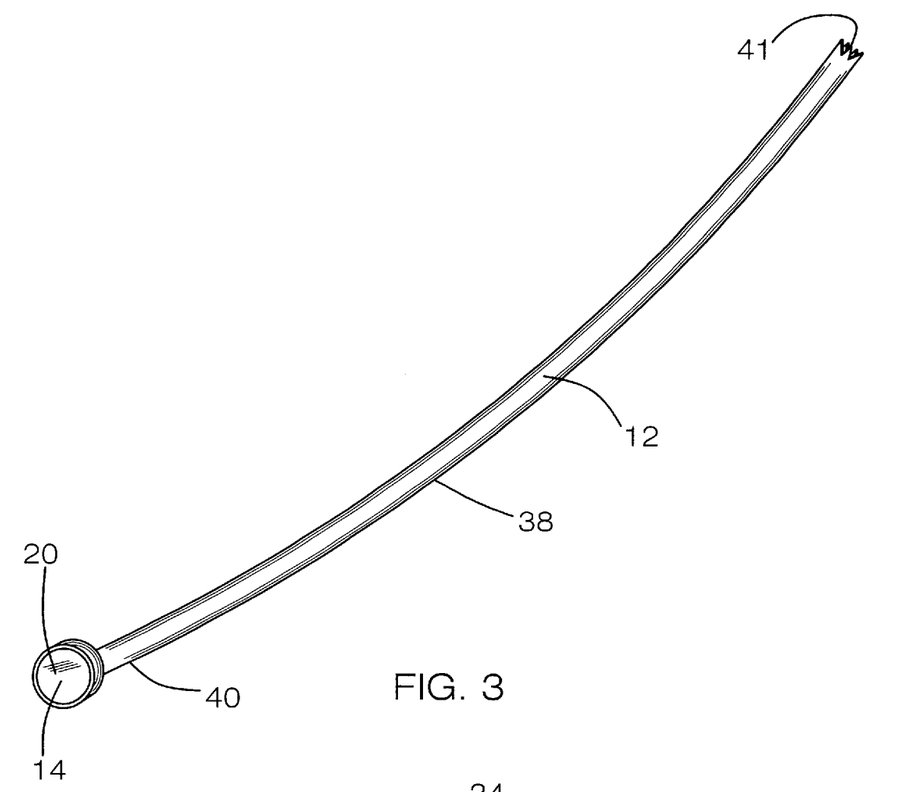
FIG. 3 is a schematic bottom view of the handle and guide members of the present invention in an assembled condition.
Figure 4:
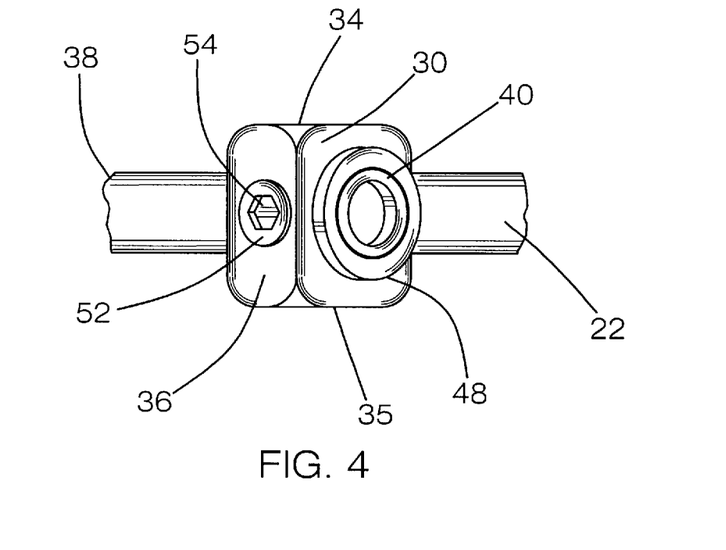
FIG. 4 is a schematic angled view of the handle and guide members in an assembled condition.
Figure 5:
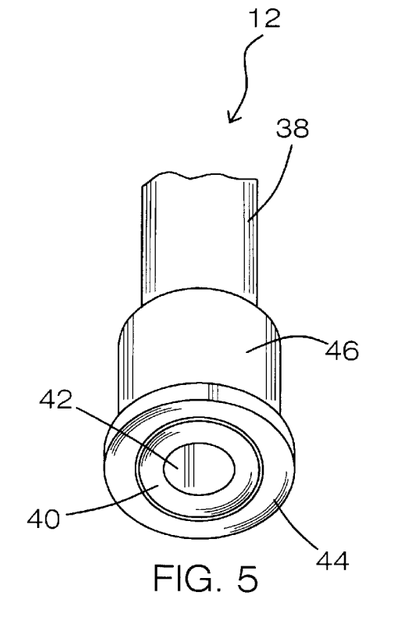
FIG. 5 is a schematic perspective end view of the base end of the guide member.
Figure 6:
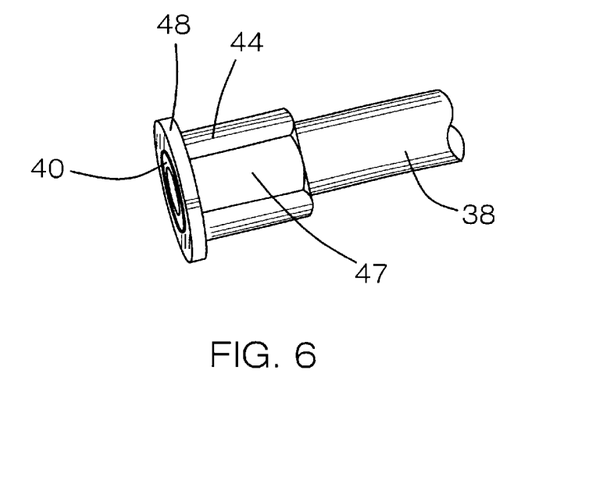
FIG. 6 is a schematic side view of the base end of the guide member.
Figure 7:
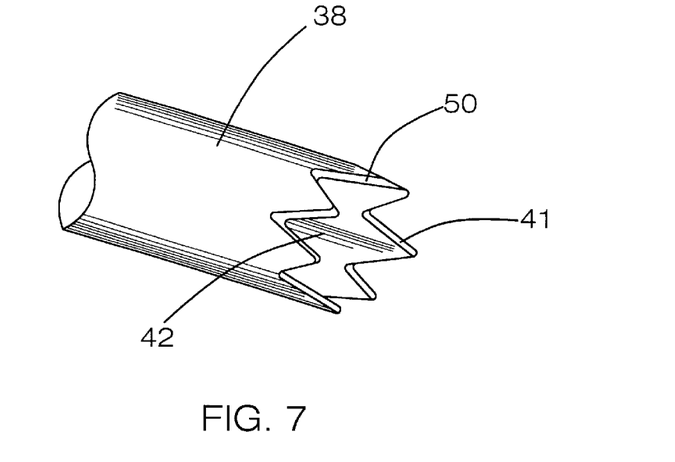
FIG. 7 is a schematic perspective view of the free end of the guide member.
Figure 8:
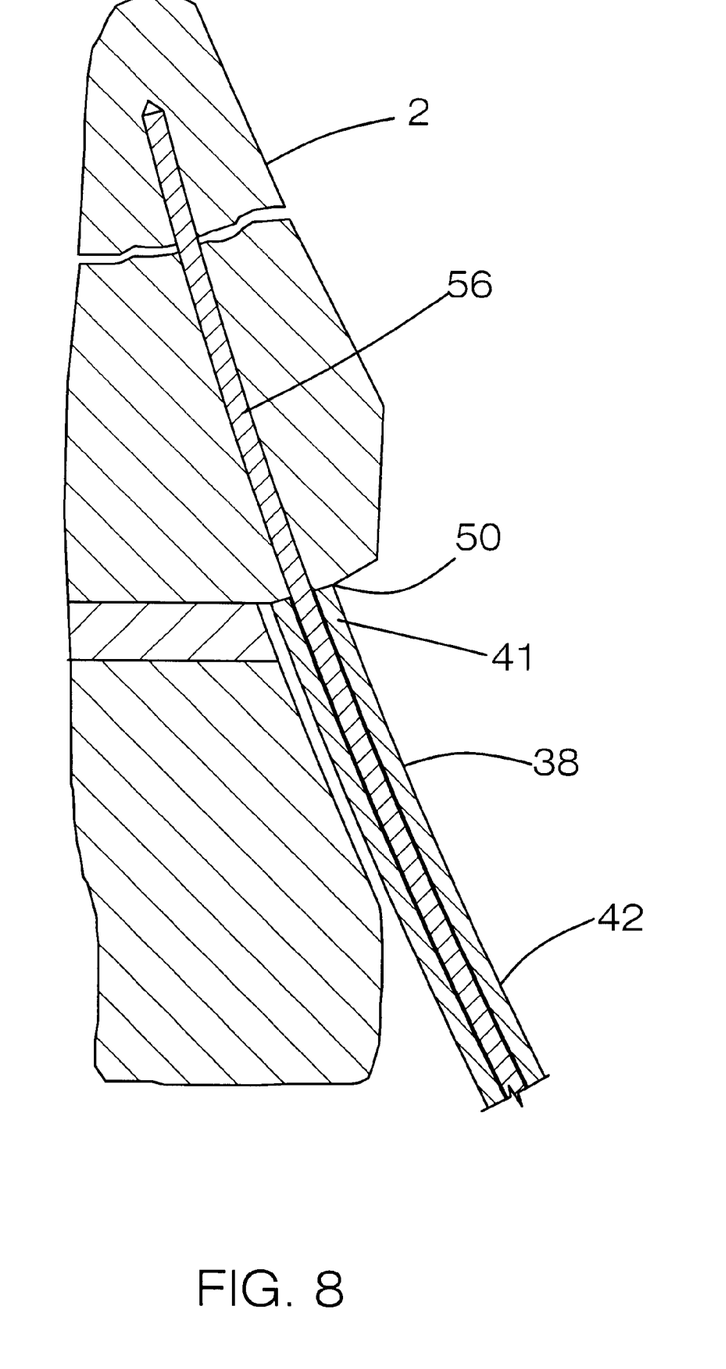
FIG. 8 is a schematic side sectional view of a portion of the neck area of a patient showing the drill guide of the invention in relation to the second and third cervical vertebra area of the patient during use of the drill guide.

With reference now to the drawings, and in particular to FIGS. 1 through 8 thereof, a new curved drill guide system embodying the principles and concepts of the present invention and generally designated by the reference numeral 10 will be described.

The invention provides a system for forming a channel in a vertebra of a patient, especially the second cervical vertebra 2 (see FIG. 8) and the odontoid process of a patient for receiving a screw to secure a fractured odontoid process in a suitable position on the body of the second cervical vertebra.

The drill guide device 10 of the invention is provided for guiding a flexible drill bit through an incision in the body of the patient and orienting the drill bit properly for drilling the channel in the second cervical vertebra. The drill guide device generally includes a guide member 12 and an elongate handle member 14 that is removably mountable on the guide member.

The elongate handle member 14 is provided for being held by the hand of a surgeon for positioning and steadying the guide member during the formation of a channel for the anterior screw fixation. The handle member 14 includes a mounting aperture that extends through the handle member 14 for receiving a portion of the guide member 12 therethrough. The mounting aperture 16 preferably has an axis that is oriented substantially perpendicular to a longitudinal axis of the handle member 14, so that the guide member 12 is oriented generally perpendicular to the handle member when the guide member is inserted in the mounting aperture. The handle member 14 has a first end 18 and a second end 19, and the mounting aperture is preferably located adjacent to the second end of the handle member.

One preferred embodiment of the handle member 14 includes a gripping portion 20 and an attachment portion 22. The gripping portion 20 may be located adjacent to the first end 18 of the handle member. The gripping portion 20 is adapted for being gripped by the hand, and preferably has an outer surface 24 with a portion of the outer surface being knurled. Illustratively, the gripping portion comprises approximately two-thirds of a length of the handle member.

The attachment portion 22 of the handle member 14 is located adjacent to the second end 19 of the handle member. Preferably, the mounting aperture 16 is formed in the attachment portion. The attachment portion 22 may comprise a shaft section 26 and a mounting section 28. The shaft section 26 extends between the gripping portion 20 and the mounting section 28. Optionally, the shaft section may have a cylindrical outer surface having a diameter approximately one-third of the diameter of the gripping portion for easy gripping by the fingertips of the surgeon's hand.

The mounting section 28 of the attachment portion may have a pair of major faces 30, 32 with the mounting aperture extending through each of the major faces. Each of the major faces 30, 32 may be substantially planar. Further, the mounting section may have a pair of side faces 34, 35 and an end face 36 extending between the pair of major faces 30, 32. The surface of each of the side faces 34, 35 may be convex between the major faces to provide a more rounded profile for the end of the handle member.

The guide member 12 is provided for removably receiving and guiding the flexible drill bit in the patient's body. The guide member includes a guide tube 38 having a base end 40 and a free end 41 and a length defined therebetween. The guide tube 38 is adapted to be removably inserted into the mounting aperture 16 of the handle member 14. A bore 42 extends along the length of the guide tube, and the bore is open at the base 40 and free 41 ends.

The guide member 12 also preferably includes a collar 44 mounted on the guide tube adjacent to the base end of the guide tube. The collar 44 is removably insertable into the mounting aperture 16 of the handle member. Preferably, the collar 44 has a larger outer surface dimension than the guide tube 38 to permit a relatively more snug relationship with the mounting aperture than the guide tube. In one preferred embodiment of the invention, the collar at least one flat 46, or planar surface, and most preferably has a pair of opposite flats 46, 47, or planar surfaces, that lie in parallel planes. The collar 44 may have arcuate surfaces extending between the flats.

A flange 48 is preferably mounted on the guide tube 38 at the base end 40. The flange 48 has a size that prevents movement of the flange through the mounting aperture 16 of the handle member. The flange is preferably located between an end of the guide member and the collar such that the collar is positioned in the mounting aperture when the guide member is inserted in the mounting aperture and the handle member is abutted against the flange. Illustratively, the collar and the flange may comprise a single piece that is mounted on the base end 40 of the guide tube.

A significant option of the invention is plurality of teeth 50 formed on the guide tube 38 for engaging a surface of the second cervical vertebra of the patient. The teeth 50 extend from the free end 41 of the guide tube 4 in a longitudinal direction from the free end of the guide tube such that the teeth are adapted for securing the free end against lateral movement relative to the surface of the vertebra when the teeth are pressed against the surface. Illustratively, the plurality of teeth comprises six teeth extending about the circumference of the tube, and each of the teeth has a substantially triangular shape.

Critically, the guide tube has an arcuate shape along the length of the guide tube 38. Preferably, the arcuate shape is substantially uniform between the base 40 and free 41 ends of the guide tube. In one preferred embodiment of the invention, the arcuate shape of the guide tube has a radius of curvature of approximately 300 mm, although radii between approximately 250 mm and 350 mm may be used.

A set screw hole 52 may be formed in the handle member for permitting securing of the guide tube in the mounting aperture. The set screw hole 52 is in communication with the mounting aperture 16. The set screw hole may be formed in the end face 36 of the mounting section of the attachment portion. A set screw 54 is threadedly mounted in the set screw hole for advancing into the mounting aperture 16 for abutting the collar 44 of the guide member 12.

Preferably, the arcuate guide tube 38 lies in a first plane. At least one flat of the collar 44 may be located in a plane oriented substantially parallel to the first plane. Also, the handle member is adapted to extend in a direction perpendicular to the plane of the guide tube when the handle member is mounted on the guide tube. This may be achieved by proper relative positioning of the set screw hole and at least one flat on the collar. The inclusion of two opposite flats 46, 47 permits the handle member to be selectively oriented in opposite directions for convenient gripping by left- and right-handed users.

The drill guide system may also include a flexible drill bit 56 of a suitable size and length for insertion through the bore 42 of the guide tube 38 for drilling the channel in the body and odontoid process of the second cervical vertebra. The flexibility of the drill bit 56 permits the bit to be inserted into the bore at the base end 40 of the guide tube follow the curvature of the bore through the tube, and exit the free end of the guide tube in the direction of the guide tube at the free end.

In use, the curved grill guide is inserted into a cavity that has been formed in the neck of the patient. A surface of the second cervical vertebra may be prepared for the drilling of the channel by removal of a portion of the second cervical vertebra. The free end 41 of the guide tube 38 of the invention (see FIG. 8) is positioned against the surface of the second. cervical vertebra with the guide tube 38 lying essentially in the sagittal anatomical plane of the spine of the patient. When in position, the portion of the guide tube 38 adjacent to the free end 41 extends generally parallel to the spine of the patient. As the guide tube 38 extends inferiorly from the second cervical vertebra, the base end 40 of the guide tube curves anteriorly away from the spine of the patient.

Significantly, positioning of the serrated teeth 50 on the free end 41 of the guide tube 38 against the surface of the second cervical vertebra functions to resist slippage of the free end with respect to the surface of the second cervical vertebra during the drilling procedure. Further facilitating the use of the drill guide 10 is the surgeon's ability to shift the position of the handle member with respect to the guide member so that the handle member may extend in a left or right lateral direction from the guide member for gripping by the preferred hand of the surgeon. Once the drilling of the channel using the curved drill guide has been performed, the drill may be removed and the screw may be inserted free hand without further assistance of the drill guide.

In one highly preferred example of the invention, the guide tube has a length of approximately 170 mm, and an outer diameter of approximately 6 mm and an inner diameter of approximately 3 mm. The guide tube has a radius of curvature of approximately 320 mm and extends over an approximately 30 degree arc. The collar of the guide member has a diameter of approximately 8 mm (with the diameter of the mounting aperture of the handle member being slightly larger), and the flange has a diameter of approximately 9 mm. The handle member has a length of approximately 150 mm, The gripping portion of the handle member has a length of approximately 100 mm and a diameter of approximately 14 mm, and the shaft section has a diameter of approximately 35 mm. The thickness of the mounting section between the major faces is approximately 6 mm.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A drill device for guiding a flexible drill bit in forming a channel in a vertebra of a patient for receiving a screw, the device comprising:

an elongate handle member for being held by a hand, a mounting aperture extending through the handle member;

a guide member for removably receiving and guiding the flexible drill bit, the guide member comprising a guide tube being removably insertable into the aperture of the handle member, the guide tube having a base end and a free end and a length therebetween, a bore extending along the length of the guide tube and opening at the base and free ends, the guide tube having an arcuate shape, the guide tube arcing in a first plane;

securing means for removably securing the elongate handle member in a position on the guide member in which the longitudinal axis of the elongate handle member is oriented substantially perpendicular to the first plane of the guide tube.

2. The device of claim 1 wherein the handle member has a first end and a second end, the mounting aperture being located adjacent to the second end of the handle member.

3. The device of claim 2 wherein the handle member comprises a gripping portion and an attachment portion; the gripping portion being located adjacent to the first end of the handle member and the attachment portion is located adjacent to the second end of the handle member, the mounting aperture being formed in the attachment portion.

4. The device of claim 3 wherein the gripping portion of the handle portion has an outer surface with a portion of the outer surface being knurled.

5. The device of claim 3 wherein the attachment portion has a pair of major faces, the mounting aperture extending through each of the major faces.

6. The device of claim 5 wherein each of the major faces is substantially planar.

7. The device of claim 1 wherein the guide member includes a collar mounted on the guide tube adjacent to the base end of the guide tube, the collar being removably insertable into the mounting aperture of the handle member.

8. The device of claim 7 wherein the securing means comprises a pair of opposite flats on the collar.

9. The device of claim 1 wherein the guide member includes a flange mounted on the base end of the guide tube, the flange having a size preventing movement of the flange through the mounting aperture of the handle member.

10. The device of claim 9 wherein the guide member includes a collar mounted on the guide tube adjacent to the base end of the guide tube, the flange being located between an end of the guide member and the collar for positioning the collar in the mounting aperture when the handle member is abutted against the flange.

11. The device of claim 1 wherein the guide tube includes a plurality of teeth formed on the guide tube for engaging a surface of a second cervical vertebra, the teeth extending from the free end of the guide tube in a longitudinal direction from the free end of the guide tube.

12. The device of claim 1 wherein the arcuate shape of the guide tube having a radius of curvature measuring between approximately 250 mm and approximately 350 mm.

13. The device of claim 1 wherein the securing means comprises a set screw hole formed in the handle member and in communication with the mounting aperture, and a set screw threadedly mounted in the set screw hole for advancing into the mounting aperture abut against the guide member when the guide member is inserted through the mounting aperture.

14. The device of claim 13 wherein the guide member has at least one flat against which the set screw is abuttable, the handle member extending in a direction perpendicular to the first plane of the guide tube when the set screw is abutted against the flat.

15. The device of claim 14 wherein the guide member has a pair of the flats, and the flats are located in a plane oriented substantially parallel to the first plane.

16. The device of claim 1 wherein the securing means only functions to secure the handle member to the guide member when the longitudinal axis of the handle member is oriented substantially perpendicular to the first plane of the guide tube.

17. The device of claim 1 wherein the securing means removably secures the elongate handle member in a pair of positions in which the longitudinal axis of the elongate handle member is oriented substantially perpendicular to the first plane of the guide tube.

18. A system for forming a channel in a vertebra of a patient for receiving a screw, the system comprising:
- a flexible drill bit; and
- a drill guide device for guiding a flexible drill bit in forming the channel, the drill guide device comprising:
  an elongate handle member for being held by a hand,
    a mounting aperture extending through the handle member, the mounting aperture having an axis oriented perpendicular to a longitudinal axis of the handle member, the handle member having a first end and a second end, the mounting aperture being located adjacent to the second end of the handle member, the handle member comprising:
      a gripping portion for being gripped by the hand, the gripping portion being located adjacent to the first end of the handle member, the gripping portion having an outer surface with a portion of the outer surface being knurled, the gripping portion comprising approximately two-thirds of a length of the handle member;
      an attachment portion being located adjacent to the second end of the handle member, the mounting aperture being formed in the attachment portion;
      wherein the attachment portion comprises a shaft section and a mounting section, the shaft section extending between the gripping portion and the mounting section, the mounting section having a pair of major faces, the mounting aperture extending through each of the major faces, each of the major faces being substantially planar;
  a guide member for removably receiving and guiding the flexible drill bit, the guide member comprising:
    a guide tube adapted for removably inserting into the aperture of the handle member, the guide tube having a base end and a free end and a length therebetween, a bore extending along the length of the guide tube and open at the base and free ends;
    a collar mounted on the guide tube adjacent to the base end of the guide tube, the collar being removably insertable into the mounting aperture of the handle member, the collar having a pair of opposite flats;
    a flange being mounted on the base end of the guide tube, the flange having a size preventing movement of the flange through the mounting aperture of the handle member, the flange being located between an end of the guide member and the collar for positioning the collar in the mounting aperture when the handle member is abutted against the flange;
    a plurality of teeth formed on the guide tube for engaging a surface of a second cervical vertebra, the teeth extending from the free end of the guide tube in a longitudinal direction from the free end of the guide tube, the plurality of teeth comprising six teeth, each of the teeth being substantially triangular;
  wherein the guide tube has an arcuate shape, the arcuate shape being substantially uniform along the length of the guide tube, the arcuate shape of the guide tube having a radius of curvature between approximately 250 and approximately 350 mm;
  wherein a set screw hole is formed in the handle member and is in communication with the mounting aperture and a set screw is threadedly mounted in the set screw hole for advancing into the mounting aperture abut against the guide member inserted therethrough;
  wherein the guide tube lies in a first plane, and the handle member is adapted to extend in a direction perpendicular to the plane of the guide tube when the handle member is mounted on the guide tube, the flats of the collar each being located in a plane oriented substantially parallel to the first plane.

19. A drill guide device for guiding a flexible drill bit in forming a channel in a vertebra of a patient for receiving a screw, the device comprising:
- an elongate handle member for being held by a hand, a mounting aperture extending through the handle member, the mounting aperture having an axis oriented perpendicular to a longitudinal axis of the handle member;
- a guide member for removably receiving and guiding the flexible drill bit, the guide member comprising a guide tube adapted for removably inserting into the aperture of the handle member, the guide tube having a base end and a free end and a length therebetween, a bore extending along the length of the guide tube and open at the base and free ends;
- wherein the guide tube has an arcuate shape, the arcuate shape being substantially uniform along the length of the guide tube;
- wherein the guide member includes a collar mounted on the guide tube adjacent to the base end of the guide tube, the collar being removably insertable into the mounting aperture of the handle member; and
- wherein the collar has a pair of opposite flats.

20. A drill guide device for guiding a flexible drill bit in forming a channel in a vertebra of a patient for receiving a screw, the device comprising:
- an elongate handle member for being held by a hand, a mounting aperture extending through the handle member, the mounting aperture having an axis oriented perpendicular to a longitudinal axis of the handle member;
- a guide member for removably receiving and guiding the flexible drill bit, the guide member comprising a guide tube adapted for removably inserting into the aperture of the handle member, the guide tube having a base end and a free end and a length therebetween, a bore extending along the length of the guide tube and open at the base and free ends;

wherein the guide tube has an arcuate shape, the arcuate shape being substantially uniform along the length of the guide tube;

wherein the guide tube lies in a first plane, and the handle member is adapted to extend in a direction perpendicular to the plane of the guide tube when the handle member is mounted on the guide tube;

wherein the guide member has a pair of flats, and the flats are located in a plane oriented substantially parallel to the first plane.

* * * * *